(12) United States Patent
Uehara et al.

(10) Patent No.: US 12,059,287 B2
(45) Date of Patent: Aug. 13, 2024

(54) RADIOGRAPHING SYSTEM, RADIOGRAPHING METHOD, AND STORAGE MEDIUM

(71) Applicant: CANON KABUSHIKI KAISHA, Tokyo (JP)

(72) Inventors: Keiko Uehara, Kanagawa (JP); Hironori Yamashita, Kanagawa (JP); Masaya Kawai, Kanagawa (JP); Tomohiro Kawanishi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 268 days.

(21) Appl. No.: 17/752,641

(22) Filed: May 24, 2022

(65) Prior Publication Data

US 2022/0378393 A1   Dec. 1, 2022

(30) Foreign Application Priority Data

May 28, 2021  (JP) ................. 2021-090314

(51) Int. Cl.
*A61B 6/00* (2024.01)
*A61B 6/46* (2024.01)
*G01T 7/00* (2006.01)

(52) U.S. Cl.
CPC ............ *A61B 6/56* (2013.01); *A61B 6/465* (2013.01); *A61B 6/542* (2013.01); *G01T 7/00* (2013.01)

(58) Field of Classification Search
None
See application file for complete search history.

(56) References Cited

U.S. PATENT DOCUMENTS

| | | | |
|---|---|---|---|
| 6,201,249 B1 * | 3/2001 | Yamayoshi | A61B 6/4494 250/370.11 |
| 2008/0224047 A1 * | 9/2008 | Nakayama | G01T 1/247 250/354.1 |
| 2019/0090839 A1 | 3/2019 | Okuno | |

FOREIGN PATENT DOCUMENTS

| | | |
|---|---|---|
| EP | 2564785 A1 | 3/2013 |
| JP | 2017127444 A | 7/2017 |
| JP | 2020162971 A | 10/2020 |
| WO | 2016/032275 A1 | 3/2016 |

\* cited by examiner

*Primary Examiner* — Edwin C Gunberg
(74) *Attorney, Agent, or Firm* — Canon U.S.A., Inc. IP Division

(57) ABSTRACT

A radiographing system includes a radiation generation apparatus emitting a radiation, a radiation detection apparatus detecting the radiation to generate a radiographic image, and a radiographing apparatus controlling operation of the radiation detection apparatus by communicating with the radiation detection apparatus. The radiographing system further includes an acquisition unit configured to acquire information about the radiation detection apparatus, and a determination unit configured to determine whether the radiation detection apparatus includes an automatic exposure control (AEC) function, based on the information about the radiation detection apparatus acquired by the acquisition unit.

13 Claims, 17 Drawing Sheets

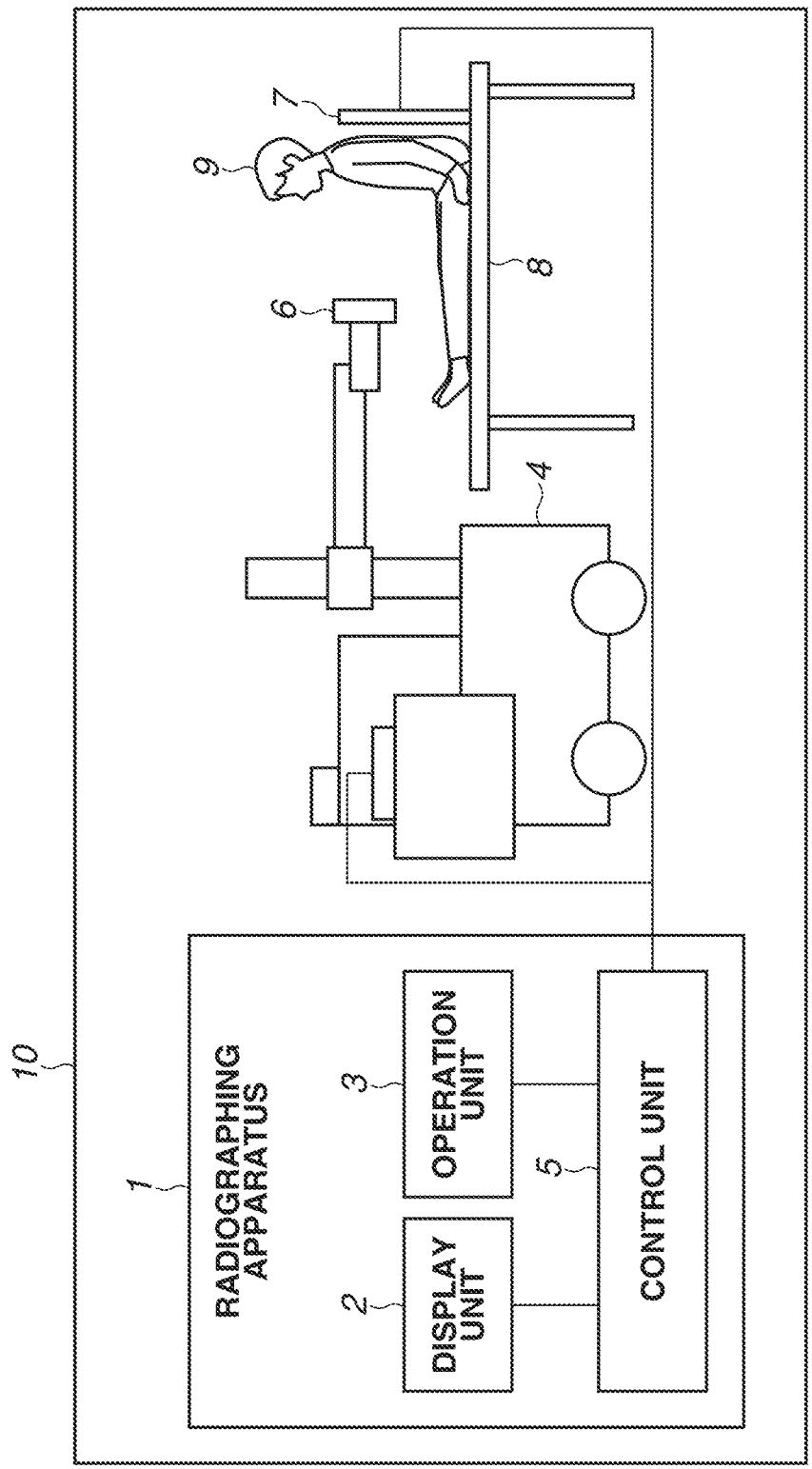

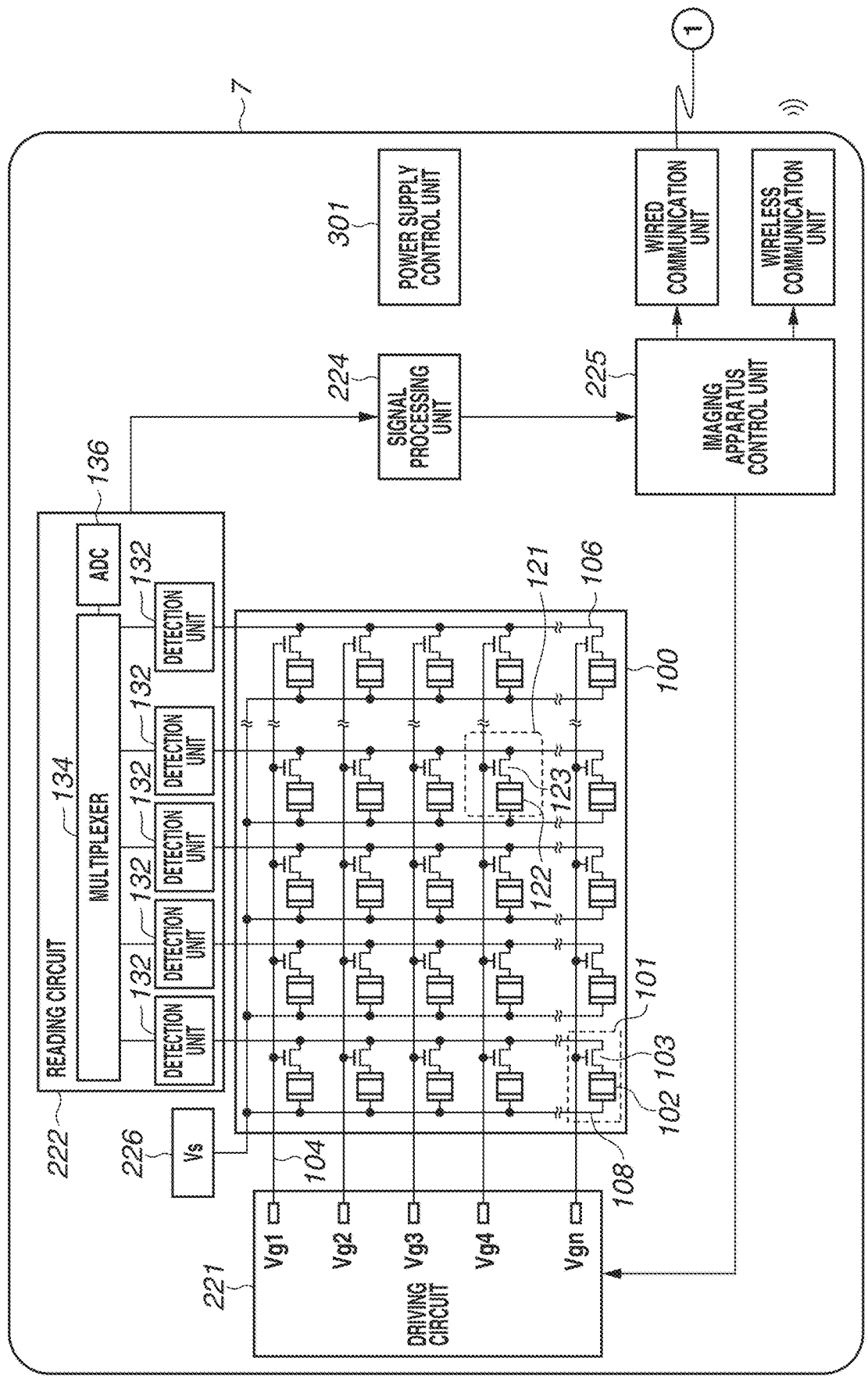

RADIOGRAPHING SYSTEM, RADIOGRAPHING METHOD, AND STORAGE MEDIUM

BACKGROUND OF THE INVENTION

Field of the Invention

The present invention relates to a radiographing system, a radiographing method, and a storage medium.

Description of the Related Art

A radiographing apparatus using a sensor panel detecting a radiation such as an X-ray is widely used in an industrial field, a medical field, and other fields. In recent years, multifunctionality of the radiographing apparatus has been studied. As one example, incorporation of a radiation irradiation monitoring function has been studied. Such a function enables, for example, detection of a timing when radiation irradiation from a radiation source is started, detection of a timing when the radiation irradiation is to be stopped, and detection of a dose or a cumulative dose of radiation. The cumulative dose of radiation passed through an examinee is detected, and irradiation of the radiation from the radiation source is stopped when the detected cumulative dose reaches an appropriate amount, thereby enabling automatic exposure control (AEC). In a case where the automatic exposure control is performed by using a flat panel detector (FPD), a plate-shaped AEC sensor separate from the FPD is typically sandwiched between an object and the FPD. The AEC sensor measures a dose of radiation passed through the object with one to five predetermined radiation detection areas (lighting fields) where the radiation is monitored, and X-ray irradiation is stopped when the measured dose reaches a predetermined dose.

In a case of imaging using the separate AEC sensor, it is sometimes difficult to carry the FPD and the AEC sensor, and thus imaging in which the FPD and the AEC are stationarily installed, like upright/recumbent position imaging is common. In a case where the FPD is internally mounted with the AEC function, the FPD becomes portable as with the existing FPD, which enables the AEC imaging in a body position other than upright position/recumbent position. In contrast, the object and the FPD have optional positional relationship or unintentional positional relationship, which makes it difficult to control exposure appropriately. As a result, a radiographic image with an appropriate density may not be acquired and reimaging may be necessary.

A method of adjusting an alignment of the object and lighting fields of the FPD is discussed in, for example, Japanese Patent Application Laid-Open Nos. 2017-127444 and 2020-162971.

Unlike a case of using the separate AEC sensor, however, it sometimes cannot be clearly determined that the FPD used for the imaging is mounted with the AEC function in a case of using the FPD internally mounted with the AEC function. Further, the techniques discussed in Japanese Patent Application Laid-Open Nos. 2017-127444 and 2020-16271 cannot detect the FPD that is not mounted with the AEC function.

The present invention is directed to, as one of the objects, a radiographing system that performs AEC imaging and that is capable of performing imaging using the AEC function as intended by a user.

The present invention is not limited to the above-described objective. The present invention is also directed to, as one of the objects, a technique realizing advantageous effects that are derived from configurations described in exemplary embodiments below but are not derived from the existing technique.

SUMMARY OF THE INVENTION

A radiographing system includes a radiation generation apparatus emitting a radiation, a radiation detection apparatus detecting the radiation to generate a radiographic image, and a radiographing apparatus controlling operation of the radiation detection apparatus by communicating with the radiation detection apparatus. The radiographing system further includes an acquisition unit configured to acquire information about the radiation detection apparatus, and a determination unit configured to determine whether the radiation detection apparatus includes an automatic exposure control (AEC) function, based on the information about the radiation detection apparatus acquired by the acquisition unit.

Further features of the present invention will become apparent from the following description of exemplary embodiments with reference to the attached drawings.

BRIEF DESCRIPTION OF THE DRAWINGS

FIG. 1 is a block diagram illustrating an example of a radiographing system.

FIG. 2 is a block diagram illustrating an example of a detection apparatus.

DESCRIPTION OF THE EMBODIMENTS

Figure 3A:
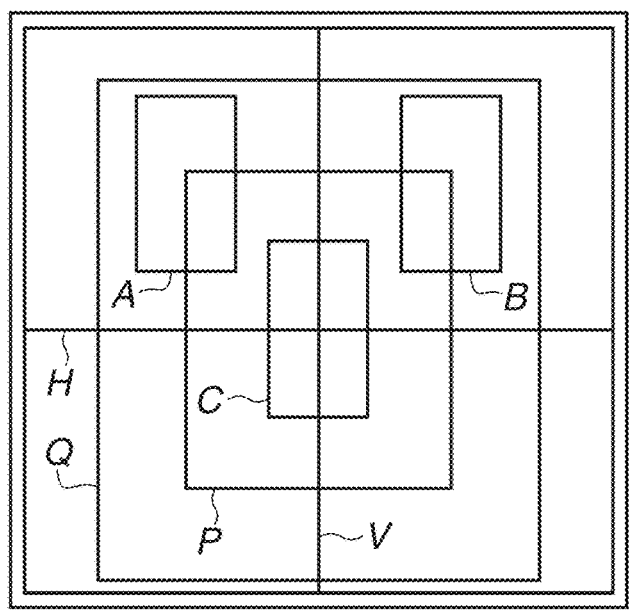
FIGS. 3A to 3C are diagrams each illustrating an example of lighting field arrangement and imaging area arrangement.

Some exemplary embodiments of the present invention are described in detail below with reference to accompanying drawings. The following exemplary embodiments do not limit the present invention according to claims, and all of combinations of characteristics described in the exemplary embodiments are not necessarily essential for solving means of the present invention. In the following exemplary embodiments and claims, examples of the radiation include, in addition to an X-ray, an α-ray, a β-ray, a γ-ray, and various kinds of particle beams.

A first exemplary embodiment of the present invention will now be described with reference to FIG. 1. FIG. 1 is a block diagram illustrating a configuration example of a radiographing system according to the first exemplary embodiment.

As illustrated in FIG. 1, a radiographing apparatus 1 performing radiography is placed in an imaging room 10. Further, a radiation generation apparatus 4 generating a radiation, a detection apparatus 7 detecting the radiation passed through an examinee 9 to capture a radiographic image, and an imaging table 8 are placed in the imaging room 10. In other words, the radiographing system includes a radiation generation apparatus configured to irradiate a radiation, a radiation detection apparatus configured to detect the radiation to capture a radiographic image and including lighting fields where automatic exposure is performed, and a control apparatus configured to control operation of the radiation detection apparatus by communicating with the radiation detection apparatus.

The radiographing apparatus 1 includes a display unit 2 displaying a radiographic image and various kinds of information, an operation unit 3 on which an operator performs operation, and a control unit 5 controlling components. The radiographing apparatus 1 further includes one or more processors and one or more memories. The processors execute programs stored in the memories to realize functional configurations of the units. The functional configurations of the units may be, however, partially or wholly realized by hardware, such as a dedicated integrated circuit, as long as similar functions are realized.

The radiation generation apparatus 4 sets a generation condition of a radiation in a radiation generation unit 6, and controls the radiation generation unit 6. The radiation generation unit 6 functions as a radiation source generating a radiation. The radiation generation unit 6 is realized by, for example, a radiation tube, and irradiates the examinee 9 (e.g., specific site of examinee 9) with the radiation.

The radiation generation unit 6 can irradiate a desired irradiation range with the radiation. An emission surface of the radiation generation unit 6 includes a diaphragm (not illustrated) blocking the radiation. The operator controls the diaphragm blocking the radiation to adjust the irradiation range irradiated with the radiation from the radiation generation unit 6.

The radiographing system includes the detection apparatus 7 detecting the radiation emitted from the radiation generation unit 6. The detection apparatus 7 detects the radiation passed through the examinee 9, and outputs image data corresponding to the radiation. The image data is also referred to as a radiographic image.

More specifically, the detection apparatus 7 detects the radiation passed through the examinee 9 as charges corresponding to a dose of the passed radiation. The detection apparatus 7 employs, for example, a direct-conversion type flat panel detector (FPD) directly converting a radiation into charges using, for example, amorphous selenium (a-Se) that converts a radiation into charges, and an indirect FPD using a scintillator (e.g., cesium iodide (CsI)) and a photoelectric conversion element (e.g., amorphous silicon (a-Si) element).

FIG. 2 is a block diagram illustrating the detection apparatus 7. As illustrated in FIG. 2, the detection apparatus 7 includes a radiation detector 100. The radiation detector 100 has a function detecting the irradiated radiation. The radiation detector 100 includes a plurality of pixels arranged to configure a plurality of rows and a plurality of columns. In the following description, an area of the radiation detector 100 where the plurality of pixels is arranged is referred to as a detection area.

The plurality of pixels includes imaging pixels 101 to acquire a radiographic image or radiation irradiation information (hereinafter, referred to as detection pixels because usage to acquire radiation irradiation information is described in the present exemplary embodiment of the present invention), and correction pixels 121 for removing a dark current component and a crosstalk component. The detection pixels 101 may be used only for acquiring the radiographic image, or may be used only for acquiring the radiation irradiation information. Further, the detection pixels 101 may be selectively used for acquiring the radiographic image or for acquiring the radiation irradiation information, or may be used for acquiring the radiographic image and for acquisition of the radiation at the same time.

Each of the detection pixels 101 includes a first conversion element 102 converting a radiation into an electric signal, and a first switch 103 disposed between a corresponding column signal line 106 and the first conversion element 102.

The first conversion element 102 includes a scintillator converting a radiation into light, and a photoelectric conversion element converting light into an electric signal. The scintillator is typically formed in a sheet shape so as to cover the detection area and is shared by the plurality of pixels. Alternatively, the first conversion element 102 includes a conversion element directly converting a radiation into light.

Figure 3B:
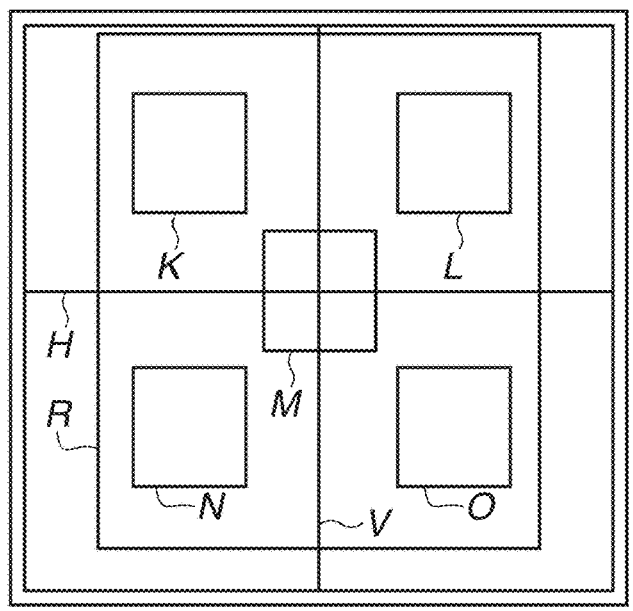
Figure 3C:
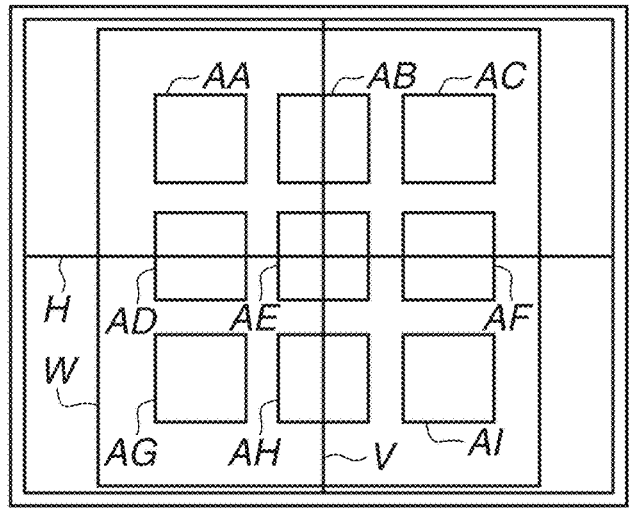

The first switch 103 includes a thin-film transistor (TFT) in which an active area is configured by a semiconductor such as amorphous silicon or polycrystalline silicon (preferably, polycrystalline silicon). An area where the detection pixels 101 and the correction pixels 121 for acquiring the radiation irradiation information are arranged is disposed at any position in the detection area of the detection apparatus 7. For example, as with an existing separate AEC sensor, the area where the detection pixels 101 and the correction pixels 121 for acquiring the radiation irradiation information are arranged may be disposed in a plurality of areas A to C in FIG. 3A, areas K to O in FIG. 3B, or areas AA to AI in FIG. 3C.

The detection apparatus 7 includes the plurality of column signal lines 106 and the plurality of driving lines 104. Each of the column signal lines 106 corresponds to one of the plurality of columns in the detection area. Each of the driving line 104 corresponds to one of the plurality of rows in the detection area. The driving lines 104 are driven by a driving circuit 221.

A first electrode of the first conversion element 102 is connected to a first main electrode of the first switch 103, and a first electrode of a second conversion element 122 is connected to a first main electrode of a second switch 123. A second electrode of the first conversion element 102 and a second electrode of the second conversion element 122 are each connected to a corresponding bias line 108. One bias line 108 extends in the column direction, and is connected in common to the second electrodes of the plurality of conversion elements 102 and 122 arranged in the column direction.

The bias lines 108 receives a bias voltage Vs from an element power supply circuit 226. The bias voltage Vs is supplied from the element power supply circuit 226. A power supply control unit 301 includes a battery and a direct current-direct current (DC-DC) converter. The power supply control unit 301 includes the element power supply circuit 226, and generates power supply for an analog circuit and power supply for a digital circuit performing, for example, driving control and communication.

The second main electrodes of the first switches 103 of the plurality of detection pixels 101 configuring one column and the second main electrodes of the second switches 123 of the correction pixels 121 configuring one column are connected to one corresponding column signal line 106. Control electrodes of the first switches 103 of the plurality of detection pixels 101 and a control electrode of the second switch 123 of the correction pixels 121 that are configuring one row are connected to one corresponding driving line 104. The plurality of column signal lines 106 is connected to a reading circuit 222. The reading circuit 222 includes a plurality of detection units 132, a multiplexer 134, and an analog-digital converter (hereinafter, AD converter) 136.

Each of the plurality of column signal lines 106 is connected to a corresponding detection unit 132 out of the plurality of detection units 132 of the reading circuit 222. One column signal line 106 corresponds to one detection unit 132. Each of the detection units 132 includes, for example, a differential amplifier. The multiplexer 134 selects the plurality of detection units 132 in a predetermined order, and supplies a signal from the selected detection unit 132 to the AD converter 136. The AD converter 136 converts the supplied signal into a digital signal and outputs the digital signal.

A signal processing unit 224 outputs information indicating irradiation of a radiation on the detection apparatus 7, based on an output of the reading circuit 222 (AD converter 136). More specifically, the signal processing unit 224 performs, for example, characteristic correction processing to remove a dark current component and a crosstalk component of the detection apparatus 7 using the correction pixels, detection of irradiation of the radiation, and calculation of a dose and a cumulative dose of radiation.

An imaging apparatus control unit 225 controls, for example, the driving circuit 221 and the reading circuit 222 based on the information from the signal processing unit 224 and a control command from the control unit.

The detection apparatus 7 is a portable cassette detection apparatus, and is carried with the radiation generation apparatus 4 to the imaging room 10 where inspection is performed.

The detection apparatus 7 attaches information (e.g., image identification (ID), imaging date, and transfer state of image data) to the image data, and transfers the information together with the image data to the radiographing apparatus 1.

The display unit 2 is composed of, for example, a liquid crystal display, and displays various kinds of information to the operator (e.g., radiological technologist or physician). The operation unit 3 includes an input unit and a designation unit (not illustrated), and enables operation of processing by the radiographing apparatus 1. The operation unit 3 includes, for example, a mouse and an operation button, and inputs various kinds of instructions from the operator to each of the components. The display unit 2 and the operation unit 3 may be integrally realized as a touch panel.

The control unit 5 of the radiographing apparatus 1 is connected to the detection apparatus 7 via a network, such as, a wireless local area network (LAN).

The image data, a control signal, and the like are transmitted and received between the control unit 5 and the detection apparatus 7. In other words, the image data of the radiography stored in the detection apparatus 7 is output (transferred) to the control unit 5 via the network.

Figure 4:
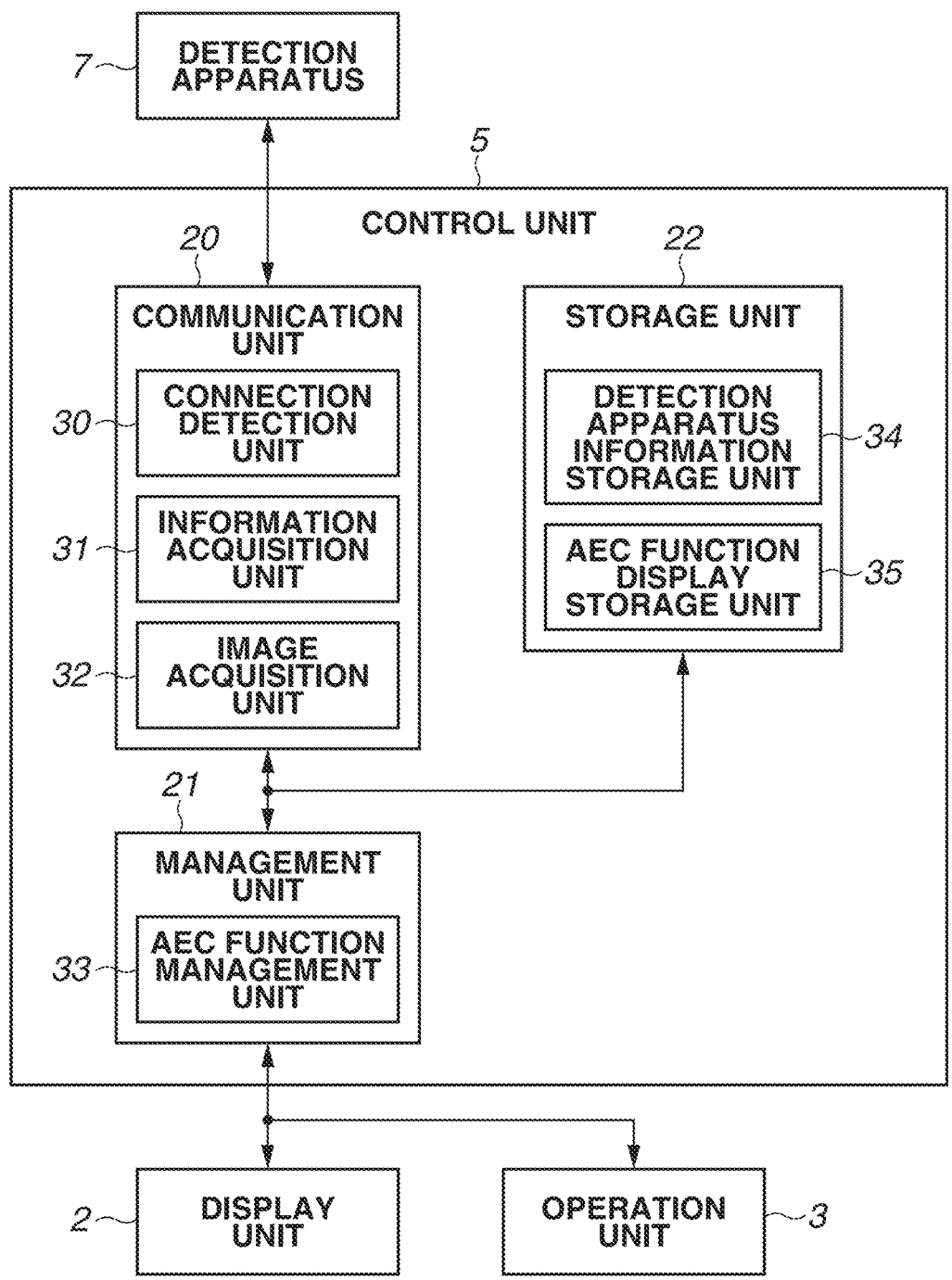
FIG. 4 is a block diagram illustrating an example of a control unit in a radiographing apparatus.

The radiographing system according to the present exemplary embodiment is described in detail with reference to FIG. 4.

The radiographing apparatus 1 includes the control unit 5 that performs image processing on the radiographic image output from the detection apparatus 7, to generate an image.

The control unit 5 includes an application function operating on a computer. The control unit 5 also controls operations of the detection apparatus 7, and outputs a radiographic image and a graphical user interface (GUI) to the display unit 2. The control unit 5 includes, as functional configurations, a communication unit 20 communicating with the detection apparatus 7, a management unit 21 managing a state of the detection apparatus 7, and a storage unit 22 storing the radiographic image output from the detection apparatus 7 and various kinds of settings of the radiographing system according to the present exemplary embodiment.

The communication unit 20 includes a connection detection unit 30, an information acquisition unit 31, and an image acquisition unit 32.

The connection detection unit 30 detects connection and disconnection of communication between the radiographing apparatus 1 and the detection apparatus 7. The information acquisition unit 31 receives information stored in the detection apparatus 7. More specifically, the information stored in the detection apparatus 7 includes information about the radiographic image and information about the detection apparatus 7. The information about the detection apparatus 7 includes, for example, a size of the detection apparatus 7 and information indicating presence/absence of an AEC function in the detection apparatus 7. The information indicating presence/absence of the AEC function in the detection apparatus 7 may be information directly indicating presence/absence of the AEC function in the detection apparatus 7. Alternatively, in a case where presence/absence of the AEC function is uniquely determined depending on, for example, a sensor name or a sensor type, the above-described items may function as the information indicating presence/absence of the AEC function in the detection apparatus 7. In the following description, the information acquisition unit 31 acquires the information about the radiographic image and the information about the detection apparatus 7. The image acquisition unit 32 acquires the radiographic image from the detection apparatus 7 that detects a radiation to capture a radiographic image.

The management unit 21 manages the information acquired by the communication unit 20, and includes an AEC function management unit 33.

The AEC function management unit 33 stores, in a detection apparatus information storage unit 34, the information about the detection apparatus 7 including the information indicating presence/absence of the AEC function in the detection apparatus 7 acquired by the information acquisition unit 31.

The AEC function management unit 33 also stores, in an AEC function display storage unit 35, display contents for a case where the detection apparatus 7 is mounted with the AEC function and display contents for a case where the detection apparatus 7 is not mounted with the AEC function, and displays presence/absence of the AEC function on the display unit 2 based on the stored contents.

The storage unit 22 includes the detection apparatus information storage unit 34 and the AEC function display storage unit 35.

The detection apparatus information storage unit 34 stores the information about the detection apparatus 7 including the information indicating presence/absence of the AEC function in the detection apparatus 7 acquired by the information acquisition unit 31.

The AEC function display storage unit 35 stores the display contents for the case where the detection apparatus 7 is mounted with the AEC function and the display contents for the case where the detection apparatus 7 is not mounted with the AEC function.

Processing by the radiographing system according to the present exemplary embodiment is described with reference to FIG. 5 and FIG. 6.

Figure 5:
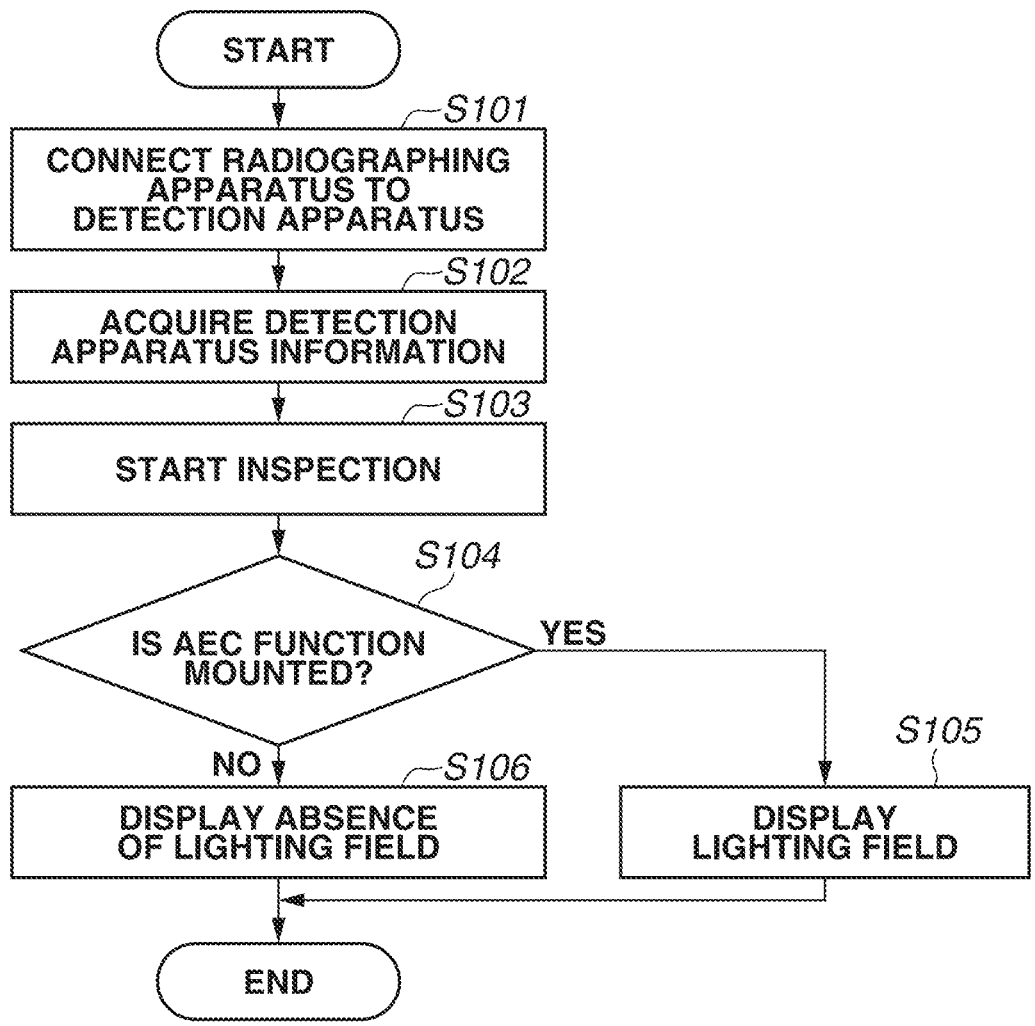
FIG. 5 is a flowchart illustrating an example of automatic exposure control (AEC) function presence/absence determination and lighting field display control.

FIG. 5 is a flowchart illustrating operation by the radiographing system according to the present exemplary embodiment.

Figure 6:
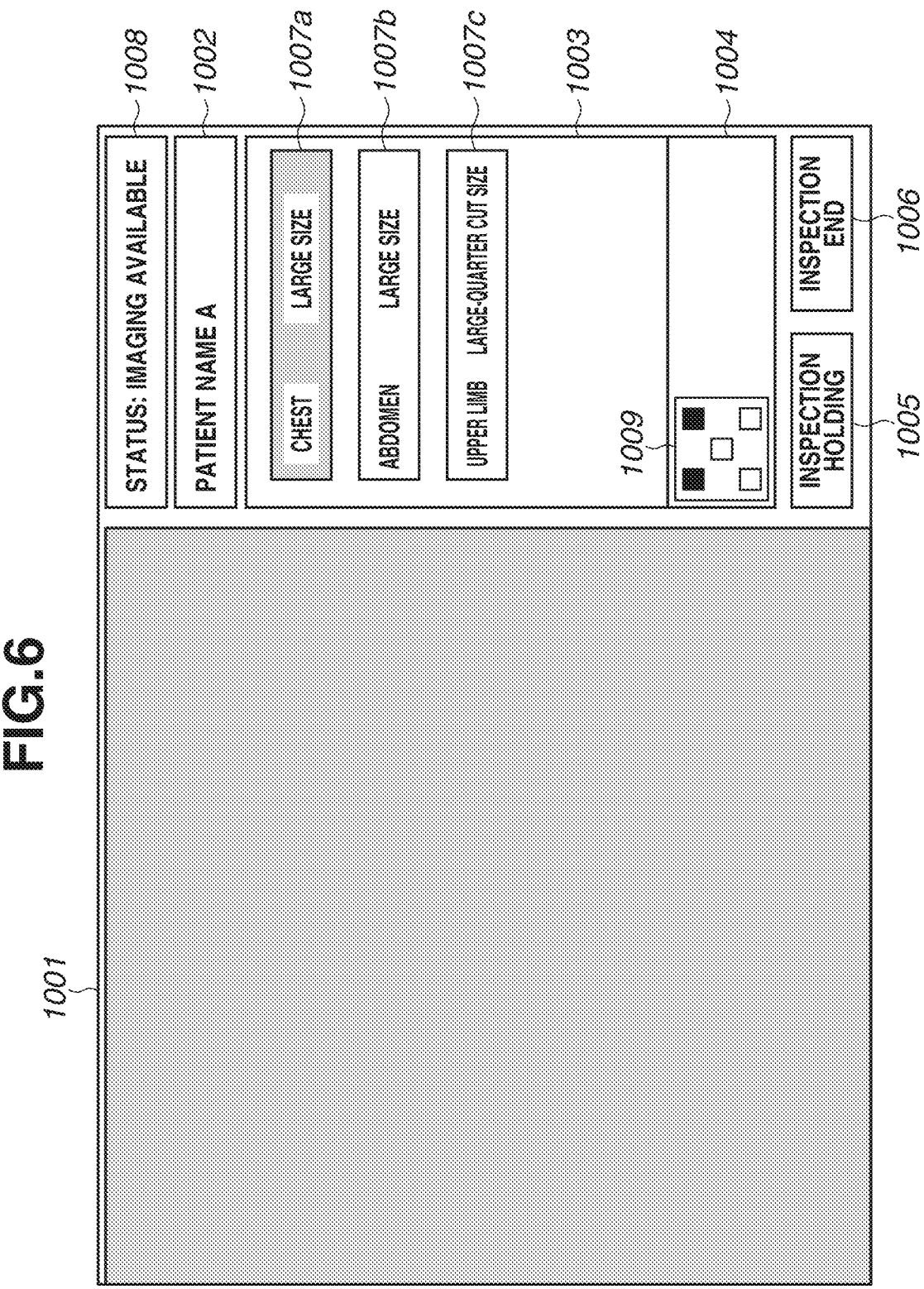
FIG. 6 is a diagram illustrating an example of a display unit in the radiographing apparatus.

FIG. 6 illustrates a display form of the display unit 2 during inspection by the radiographing system according to the present exemplary embodiment.

The display form of the display unit 2 incudes a radiographic image display field 1001, a patient information display field 1002, an imaging information display field 1003, a lighting field information display field 1004, an inspection holding instruction portion 1005, and an inspection end instruction portion 1006.

The radiographic image display field 1001 displays a captured radiographic image.

The patient information display field 1002 displays patient information.

The imaging information display field 1003 displays imaging protocols (1007a, 1007b, and 1007c in FIG. 6) each displaying a site to be captured in the inspection and the information about the detection apparatus 7. FIG. 6 illustrates, as an example, imaging protocols all using the AEC function.

The display form of the display unit 2 further includes an imaging status display field 1008 displaying current imaging availability.

The lighting field information display field 1004 includes a lighting field position display field 1009 displaying positional information on lighting fields of the connected detection apparatus 7. The positional information on the lighting fields is information indicating positions set as the lighting fields among lighting field candidates usable in the connected detection apparatus 7. As illustrated in FIG. 6, the protocol 1007a currently selected corresponds to an inspection to perform imaging a chest. Thus, for example, among five lighting field candidates, an upper left portion and an upper right portion are set as the lighting fields, and the setting is displayed as the positional information on the lighting fields.

A processing flow by the radiographic system is described.

In step S101, the radiographing apparatus 1 and the detection apparatus 7 are connected by a cable or radio. The connection detection unit 30 detects communication connection between the radiographing apparatus 1 and the detection apparatus 7.

In step S102, when the connection detection unit 30 detects the communication connection with the detection apparatus 7, the information acquisition unit 31 acquires information about the detection apparatus 7. The AEC function management unit 33 acquires the information about the detection apparatus 7 including information indicating presence/absence of the AEC function in the detection apparatus 7 through the information acquisition unit 31, in response to detection of the connection. At this time, in a case where the separate AEC sensor is used, information indicating presence of the AEC function is acquired.

In step S103, inspection is started. Thereafter, the AEC function management unit 33 acquires the display contents for the case where the detection apparatus 7 is mounted with the AEC function and the display contents for the case where the detection apparatus 7 is not mounted with the AEC function, from the AEC function display storage unit 35, and determines the contents to be displayed on the display unit 2. In step S104, the control unit 5 determines whether the detection apparatus 7 includes the AEC function, based on the information about the detection apparatus 7 including the information indicating presence/absence of the AEC function acquired by the information acquisition unit 31. In other words, the control unit 5 corresponds to a determination unit configured to determine whether the radiation detection apparatus includes the AEC function, based on information about the radiation detection apparatus acquired by an acquisition unit. The connection with the detection apparatus (step S101) and acquisition of the information (step S102) may be performed after the inspection is started (step S103).

In a case where the control unit 5 determines that the detection apparatus 7 is mounted with the AEC function (YES in step S104), the positional information on the lighting fields of the detection apparatus 7 are displayed as illustrated in the lighting field position display field 1009 in FIG. 6, in step S105. The method of displaying that the detection apparatus 7 is mounted with the AEC function is not limited to the above-described method, and is defined by an optional combination of discriminable representations, such as characters, symbols, drawings, sizes, colors, and shapes.

Figure 7:
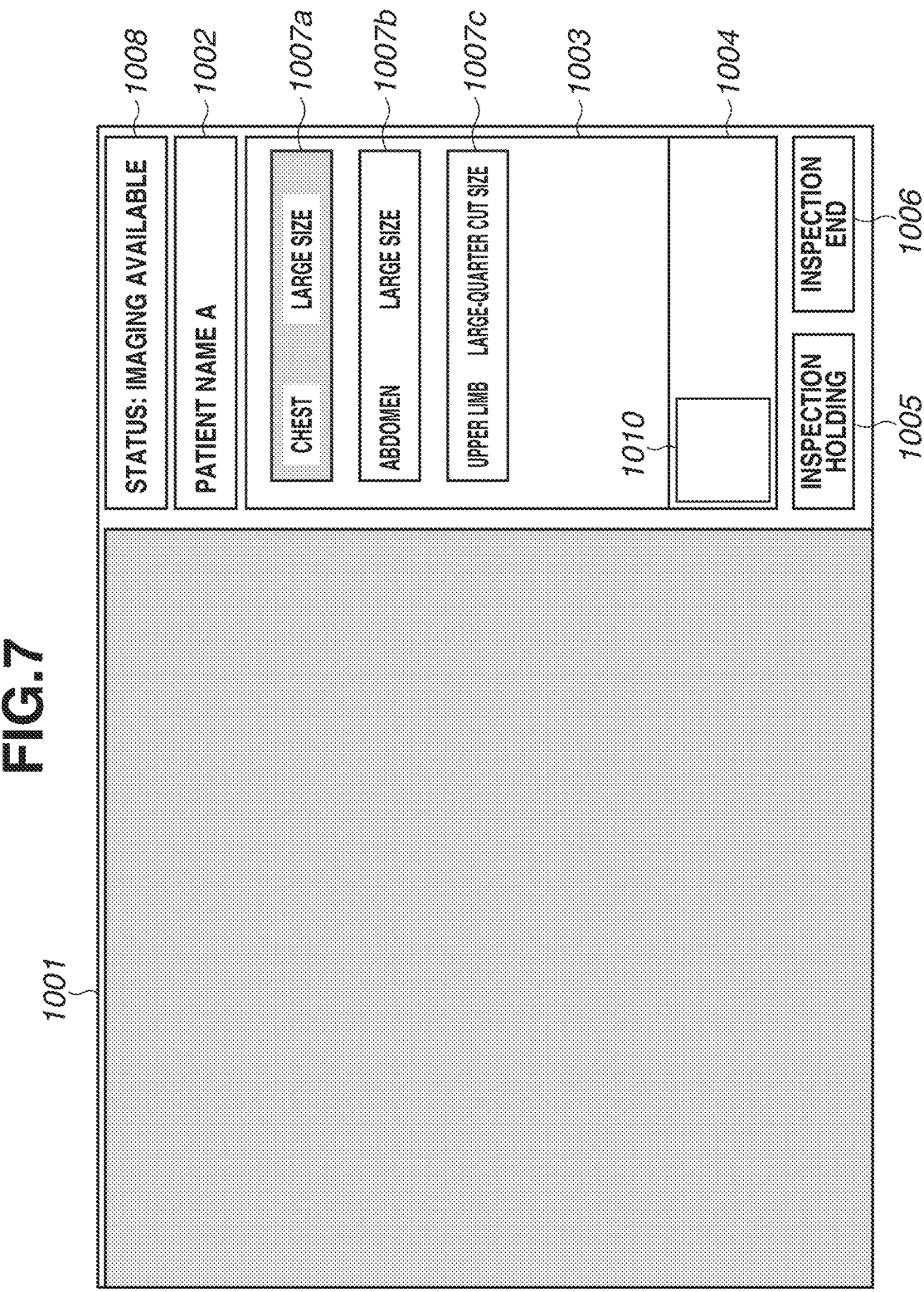
FIG. 7 is a diagram illustrating an example of the display unit in the radiographing apparatus.

In contrast, in a case where the control unit 5 determines that the detection apparatus 7 is not mounted with the AEC function (NO in step S104), the processing proceeds to step S106. In step S106, the positional information on the lighting fields is not displayed in the lighting field position display field 1009. At this time, for example, only a frame of the detection apparatus 7 may be displayed without displaying the lighting fields, as illustrated in a lighting field position display field 1010 in FIG. 7. Alternatively, nothing may be displayed in the lighting field information display field 1004.

Alternatively, display indicating the lighting fields displayed in the lighting field information display field 1004 may be grayed out. In other words, in the case where the detection apparatus 7 is not mounted with the AEC function, a notification that the AEC function is not mounted may be displayed on the display unit 2, or no information may be displayed on the display unit 2 to notify that the AEC function is not mounted, in contrast to the case where the AEC function is mounted.

The series of processing by the radiographing system according to the present exemplary embodiment is performed in the above-described manner.

According to the present exemplary embodiment, the radiographing system performing the AEC imaging can prevent the radiography erroneously performed without using the AEC function.

Further, according to the present exemplary embodiment, in the radiographing system performing the AEC imaging can provide the radiographing apparatus and the radiographing system each having a support function to perform the radiography as intended by the user.

A second exemplary embodiment will now be described.

Figure 8:
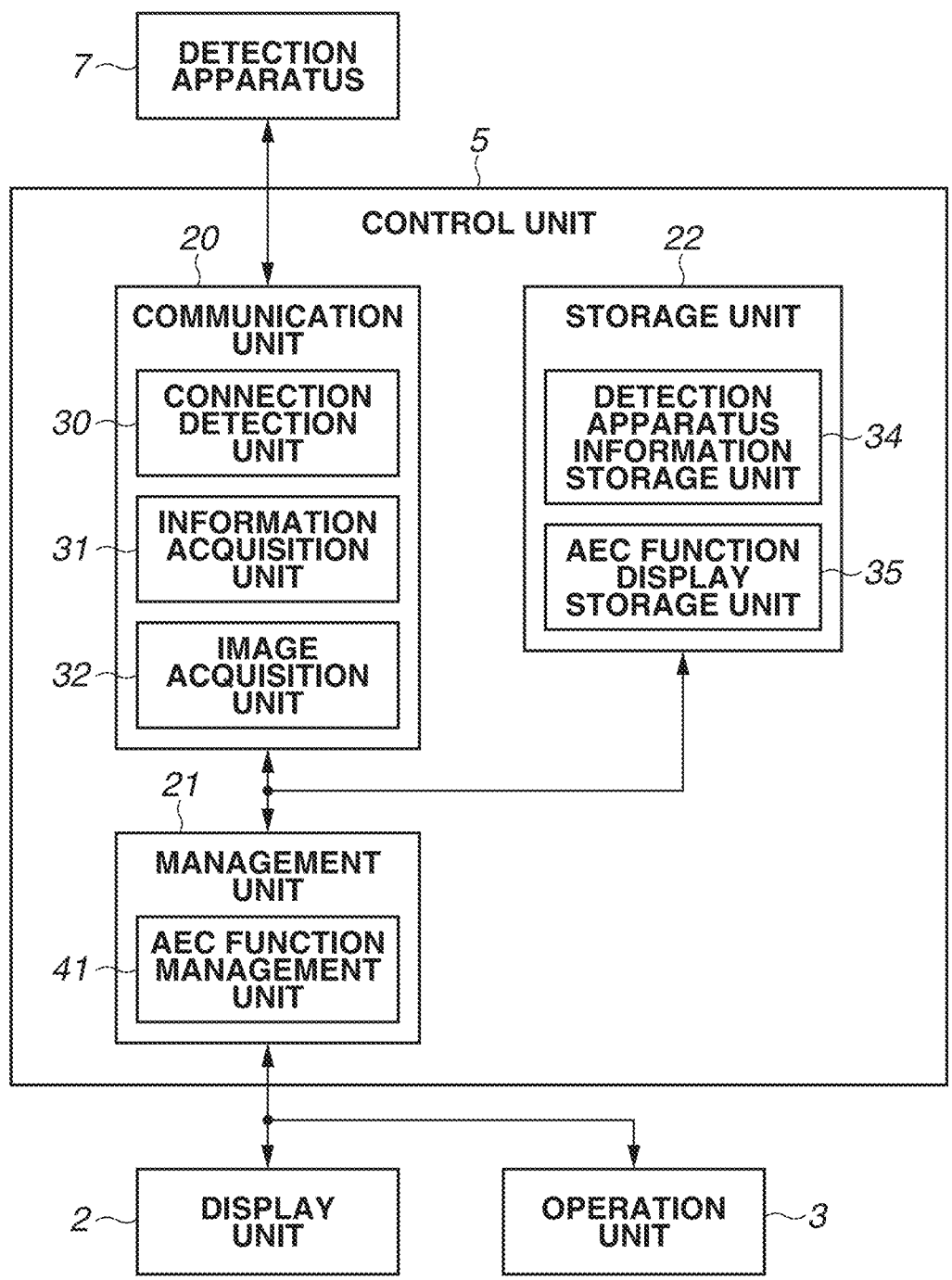
FIG. 8 is a block diagram illustrating an example of the control unit in the radiographing apparatus.

In the present exemplary embodiment, in the case where the detection apparatus 7 is not mounted with the AEC function, it is possible to notify the user that the detection apparatus 7 is not mounted with the AEC function. The second exemplary embodiment is different from the first exemplary embodiment in that an AEC function management unit 41 includes a function to display a notification on the display unit 2 as illustrated in FIG. 8, thereby notifying the user that the detection apparatus 7 is the FPD not mounted with the AEC function. The functional configurations other than the AEC function management unit 41 are similar to the functional configurations of the first exemplary embodiment, and thus description is omitted.

Figure 9:
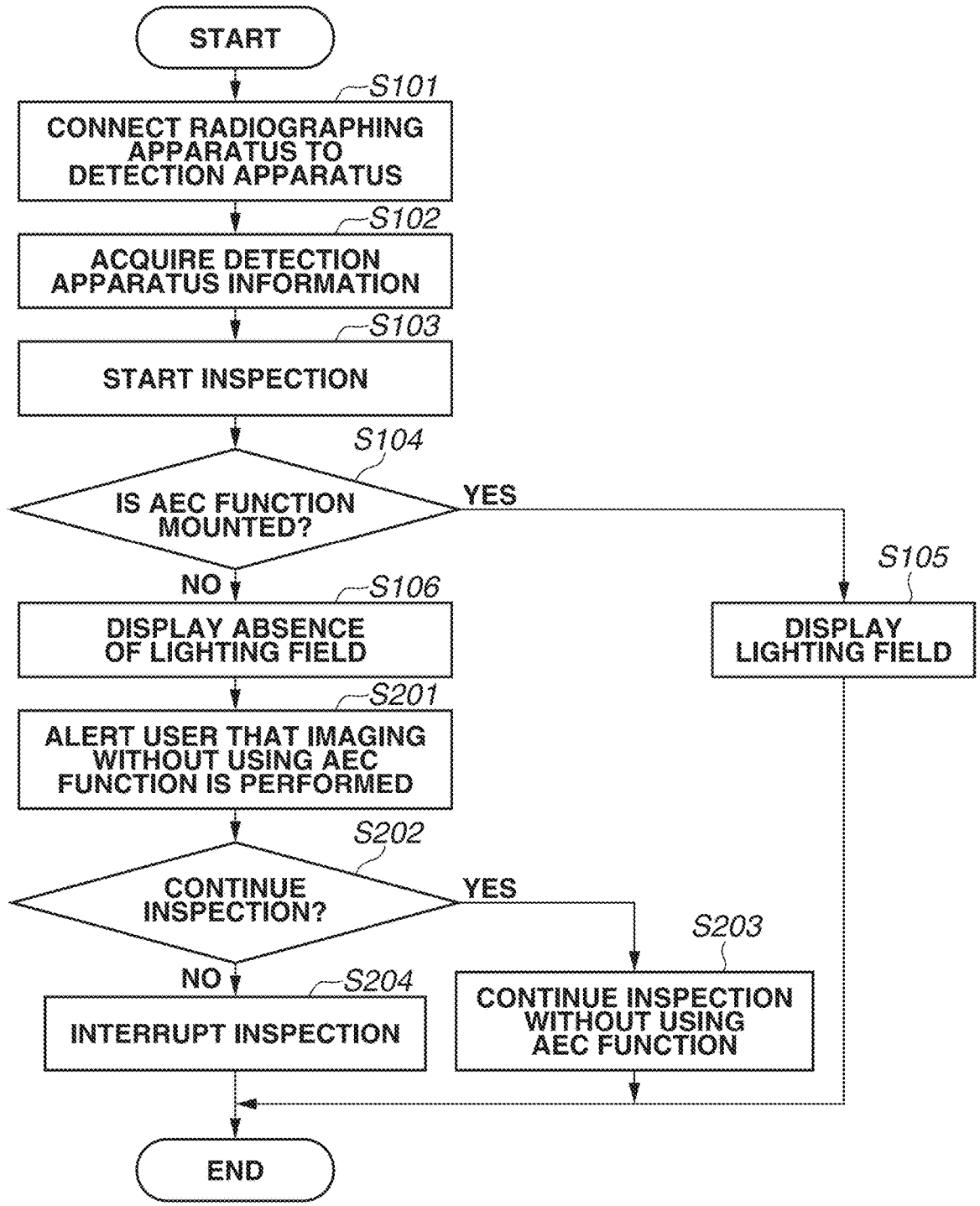
FIG. 9 is a flowchart illustrating an example of display control of an alert about the AEC function.
Figure 10:
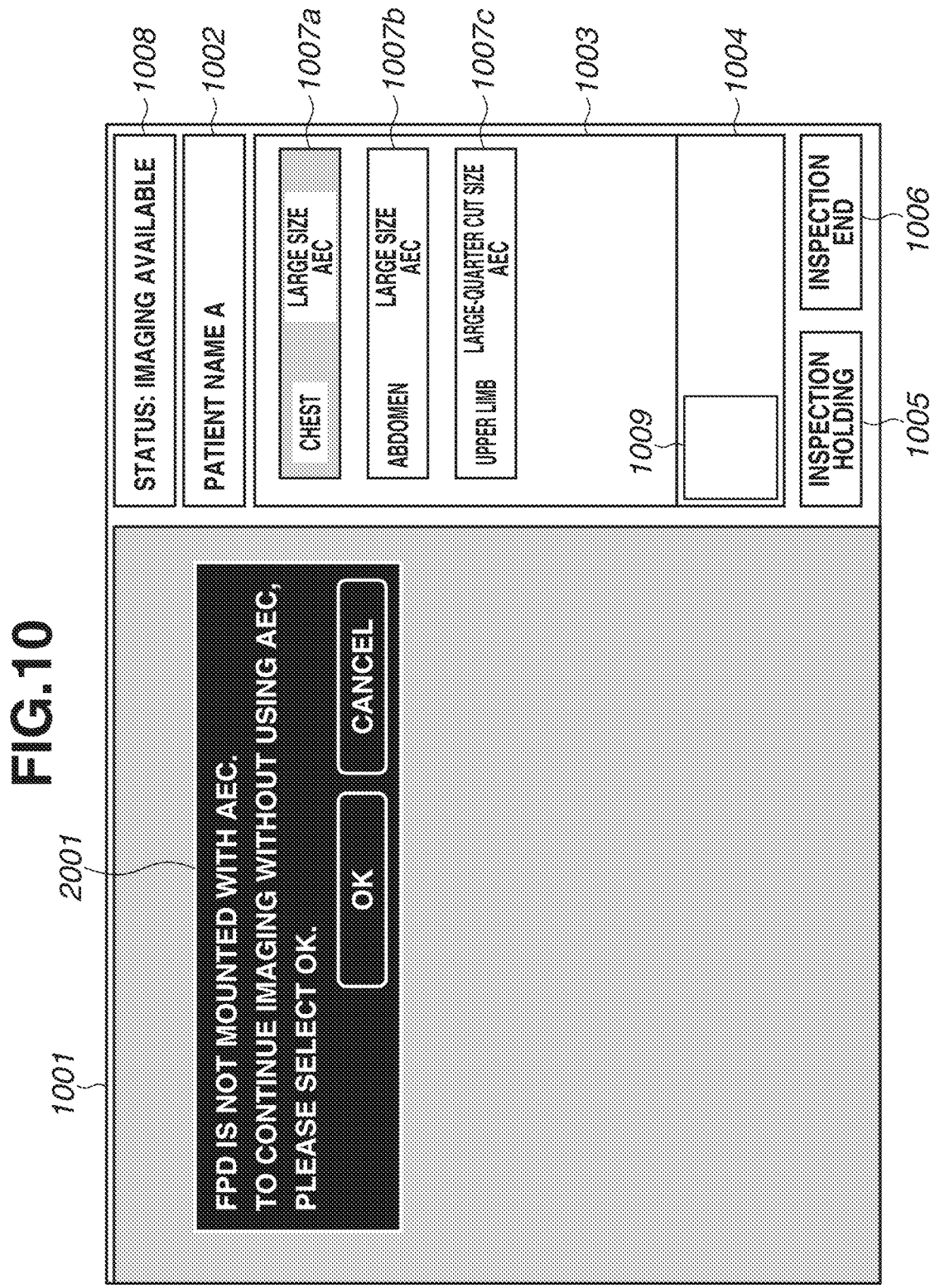
FIG. 10 is a diagram illustrating an example of the display unit in the radiographing apparatus.

Processing performed by the AEC function management unit 41 is described with reference to a flowchart in FIG. 9 and FIG. 10 illustrating a display form of the display unit 2 according to the second exemplary embodiment. The control performed before step S106 and display in the display fields 1001 to 1009 are the same as the control and the display in the first exemplary embodiment, and thus description is omitted.

In the case where the detection apparatus 7 is not mounted with the AEC function, the display unit 2 displays a notification that the AEC function is unusable. For example, as illustrated in a notification display field 2001 in FIG. 10, a message indicating that the detection apparatus 7 is not mounted with the AEC, for example, "FPD is not mounted with AEC. To continue imaging without using AEC, please select OK." is displayed, and a pop-up to select whether to continue the imaging without using the AEC is displayed in step S201. A button for a user to select continuation or interruption of the imaging may not be displayed. In other words, the AEC function management unit 41 corresponds to an example of a display control unit configured to display, in the case where it is determined that the radiation detection apparatus does not include the AEC function, a notification that the radiation detection apparatus does not include the AEC function, on the display unit. The AEC function management unit 41 also corresponds to an example of a display control unit configured to display a notification that the radiation detection apparatus does not include the AEC function, by using pop-up display. The AEC function management unit 41 further corresponds to an example of a display control unit configured to display a button to select whether to continue the imaging.

In a case where the inspection is continued (YES in step S202), the processing proceeds to step S203. In step S203, the imaging is continued without using the AEC function, and the lighting field position display field 1009 and an alert display field 2001 are hidden.

In a case where the inspection is not continued (NO in step S202), the processing proceeds to step S204. In step S204, the inspection is interrupted, and the display on the display unit 2 is transitioned to the display before start of the inspection. At this time, continuation or interruption of the inspection may be determined depending on the system. Alternatively, an OK button and a cancel button may be displayed as illustrated in FIG. 10, and the user may select continuation or interruption of the inspection. Further alternatively, the buttons illustrated in FIG. 10 may not be provided, and it may be determined based on an elapsed time.

Further, display or non-display of the notification may be settable. At this time, the setting may be determined depending on the system. Alternatively, a condition may be provided, for example, display or non-display of the notification is not displayed in a case where imaging with the same imaging information including the detection apparatus information is subsequently performed.

According to the present exemplary embodiment, in the radiographing system performing the AEC imaging, notifying the user that the FPD is not mounted with the AEC function makes it possible to reduce possibility that the imaging is erroneously performed without using the AEC function.

A third exemplary embodiment will now be described.

In the present exemplary embodiment, in the case where the detection apparatus 7 is not mounted with the AEC function, it is possible to prompt the user to switch the detection apparatus 7 to another detection apparatus mounted with the AEC function not to start the imaging.

Figure 11:
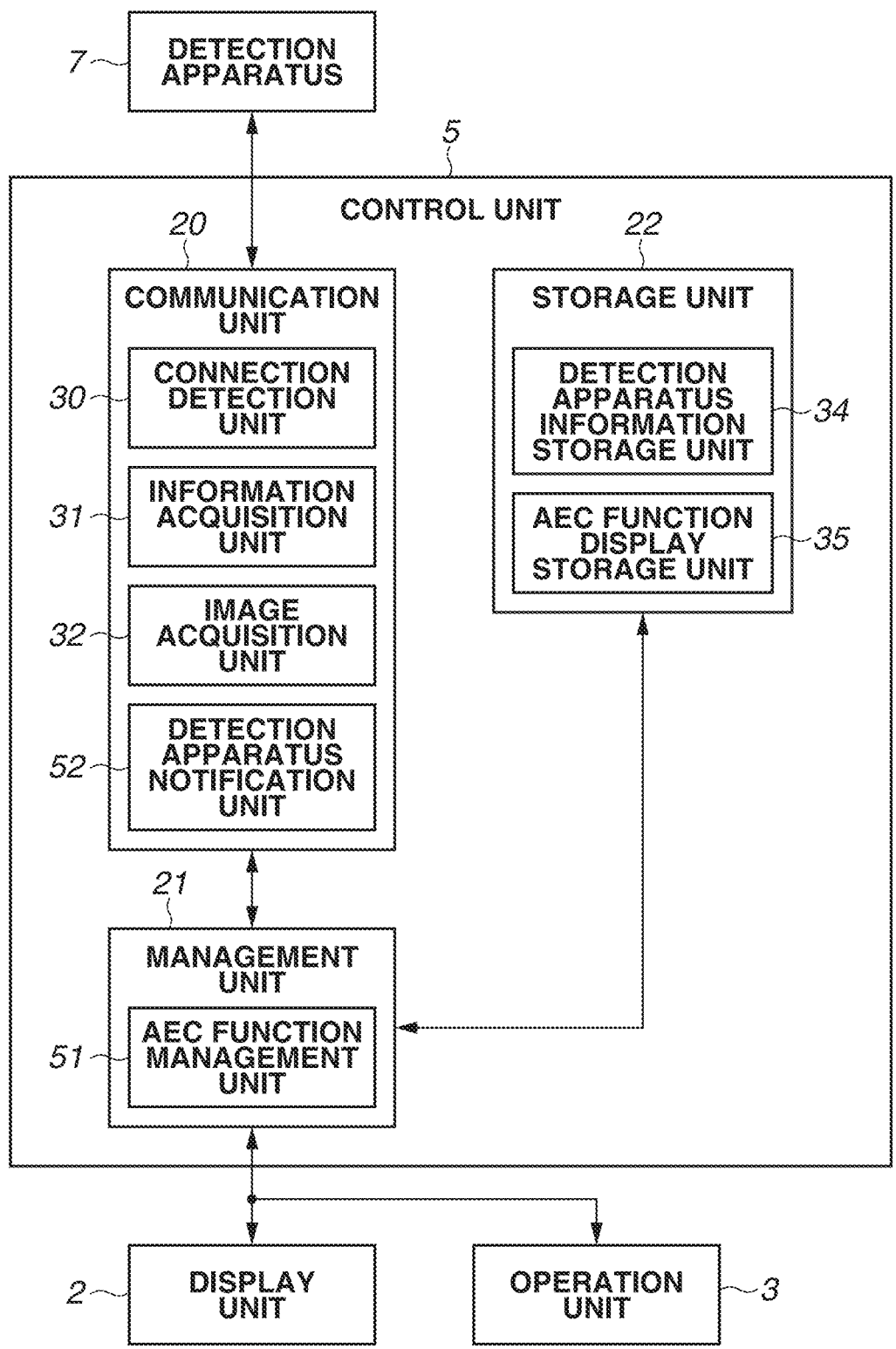
FIG. 11 is a block diagram illustrating an example of the control unit in a radiographing apparatus.

The third exemplary embodiment is different from the first and second exemplary embodiments in that an AEC function management unit 51 and a detection apparatus notification unit 52 are provided as illustrated in FIG. 11. In a case where the detection apparatus not mounted with the AEC function is used in the imaging using the AEC function, the control unit 5 can thereby notify the detection apparatus 7 that the imaging cannot be continued. The configurations other than the AEC function management unit 51 and the detection apparatus notification unit 52 are similar to the configurations in the first exemplary embodiment, and thus description is omitted.

Figure 12:
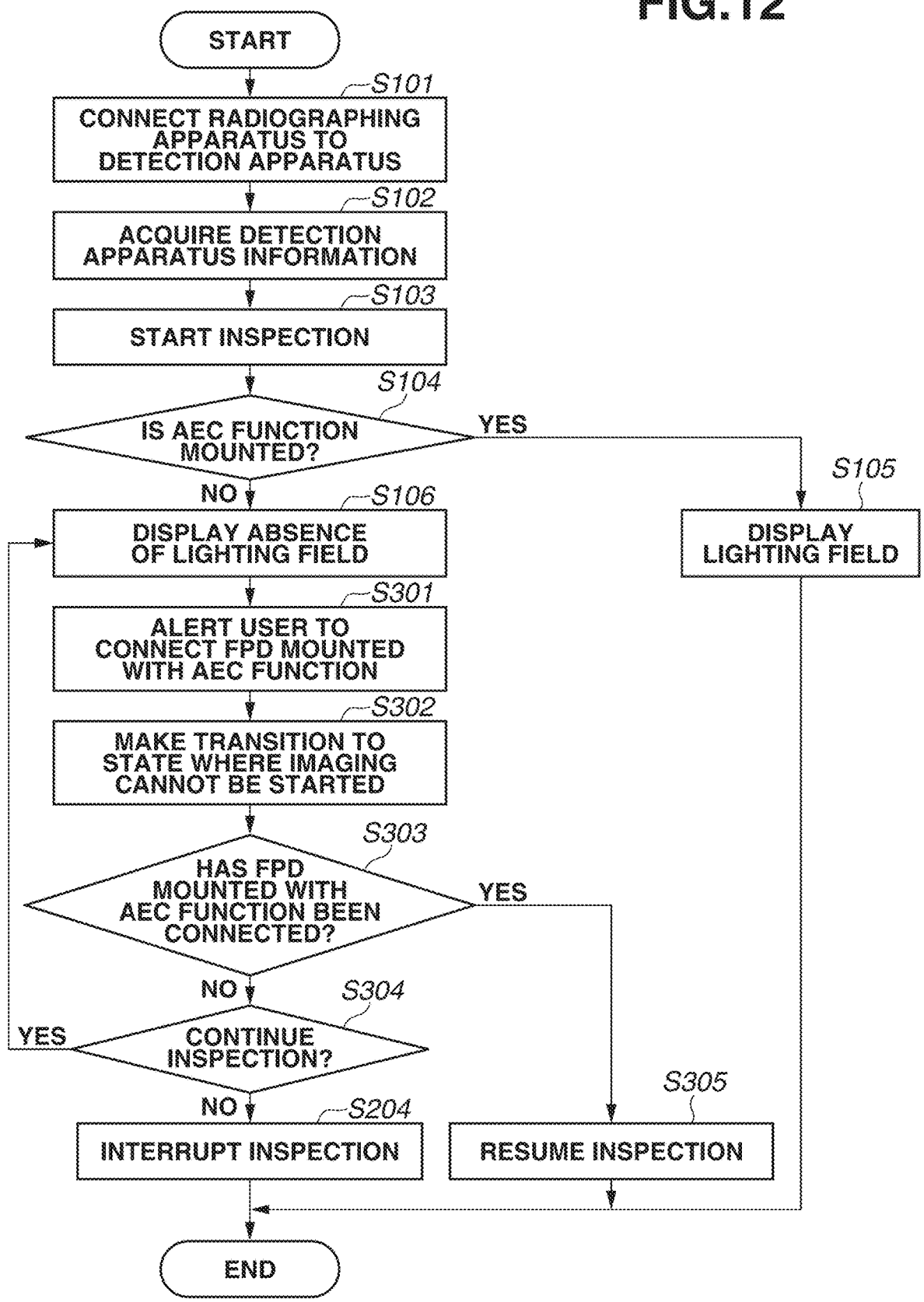
FIG. 12 is a flowchart illustrating an example of display control of an alert about the AEC function.
Figure 13:
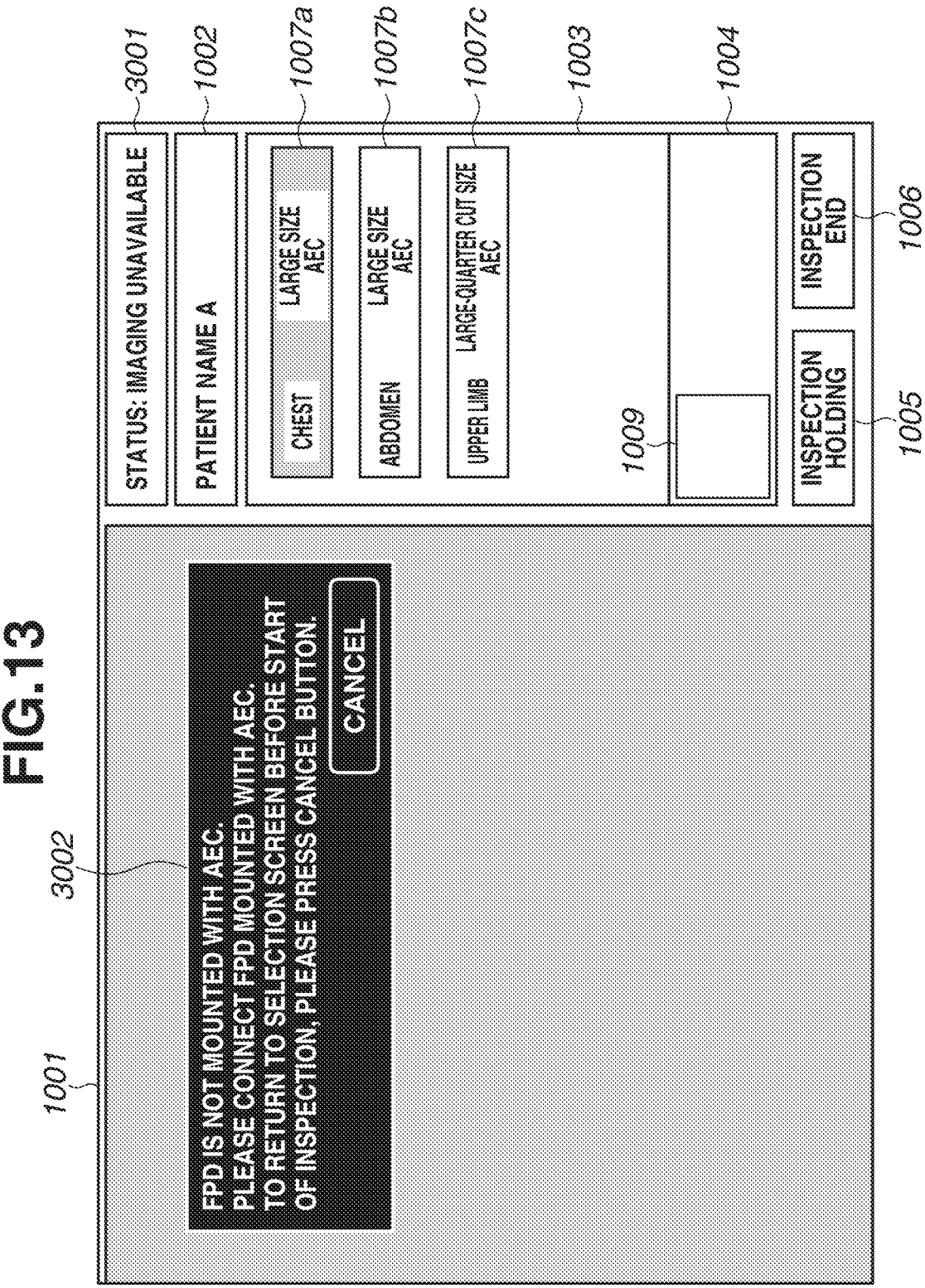
FIG. 13 is a diagram illustrating an example of the display unit in the radiographing apparatus.

Processing performed by the AEC function management unit 51 and the detection apparatus notification unit 52 is described with reference to a flowchart in FIG. 12 and FIG. 13. FIG. 13 illustrates a display form of the display unit 2 during the inspection by the radiographing system according to the third exemplary embodiment of the present invention. The control performed before step S105 and display in the display fields 1001 to 1009 are the same as the control and the display in the first exemplary embodiment, and thus description is omitted.

In step S301, a notification is displayed on the display unit 2 to alert the user to connect the detection apparatus that can use the AEC function. For example, as illustrated in an alert display field 3002 illustrated in FIG. 13, a message "FPD is not mounted with AEC. Please connect FPD mounted with AEC. To return to screen before start of inspection, please press cancel button." is displayed to notify the user that the detection apparatus 7 is not mounted with the AEC function and to alert the user to connect the detection apparatus that can use the AEC function. In step S302, the detection apparatus notification unit 52 notifies the detection apparatus 7 that the imaging is unperformable. Further, imaging unavailability is displayed in an imaging status display field 3001 illustrated in FIG. 13. In a case where the detection apparatus that can use the AEC function is connected in step S303 (YES in step S303), the detection apparatus notification unit 52 notifies the detection apparatus 7 that the imaging is performable. Further, in step S305, imaging availability is displayed in the imaging status display field 3001 illustrated in FIG. 13, and the inspection using the AEC function is started. In other words, AEC function management unit 51 corresponds to an example of a display control unit configured to display, in the case where the switched radiation detection apparatus is the detection apparatus that can use the AEC function, notification that imaging is performable. At this time, the case where the detection apparatus that can use the AEC function is connected may be a case where a detection apparatus mounted with the AEC function is connected. Alternatively, a separate AEC sensor may be used.

In a case where the inspection is continued (YES in step S304), the processing in step S106, S301, and S302 are repeated. In a case where the inspection is not continued (NO in step S304), the processing proceeds to step S204. In step S204, the inspection is interrupted, and the display on the display unit 2 is transitioned to the display before start of the inspection. At this time, continuation or interruption of the inspection may be determined depending on the system. Alternatively, a cancel button may be displayed as illustrated in FIG. 13, and the user may select continuation or interruption of the inspection. Further alternatively, the button illustrated in FIG. 13 may not be provided, and it may be determined based on an elapsed time.

According to the present exemplary embodiment, in the case where the detection apparatus 7 is not mounted with the AEC function, prompting the user to switch the detection apparatus 7 to the detection apparatus mounted with the AEC function makes it possible to reduce possibility that the imaging is performed while the FPD not mounted with the AEC function is erroneously used.

A fourth exemplary embodiment will now be described.

Figure 14:
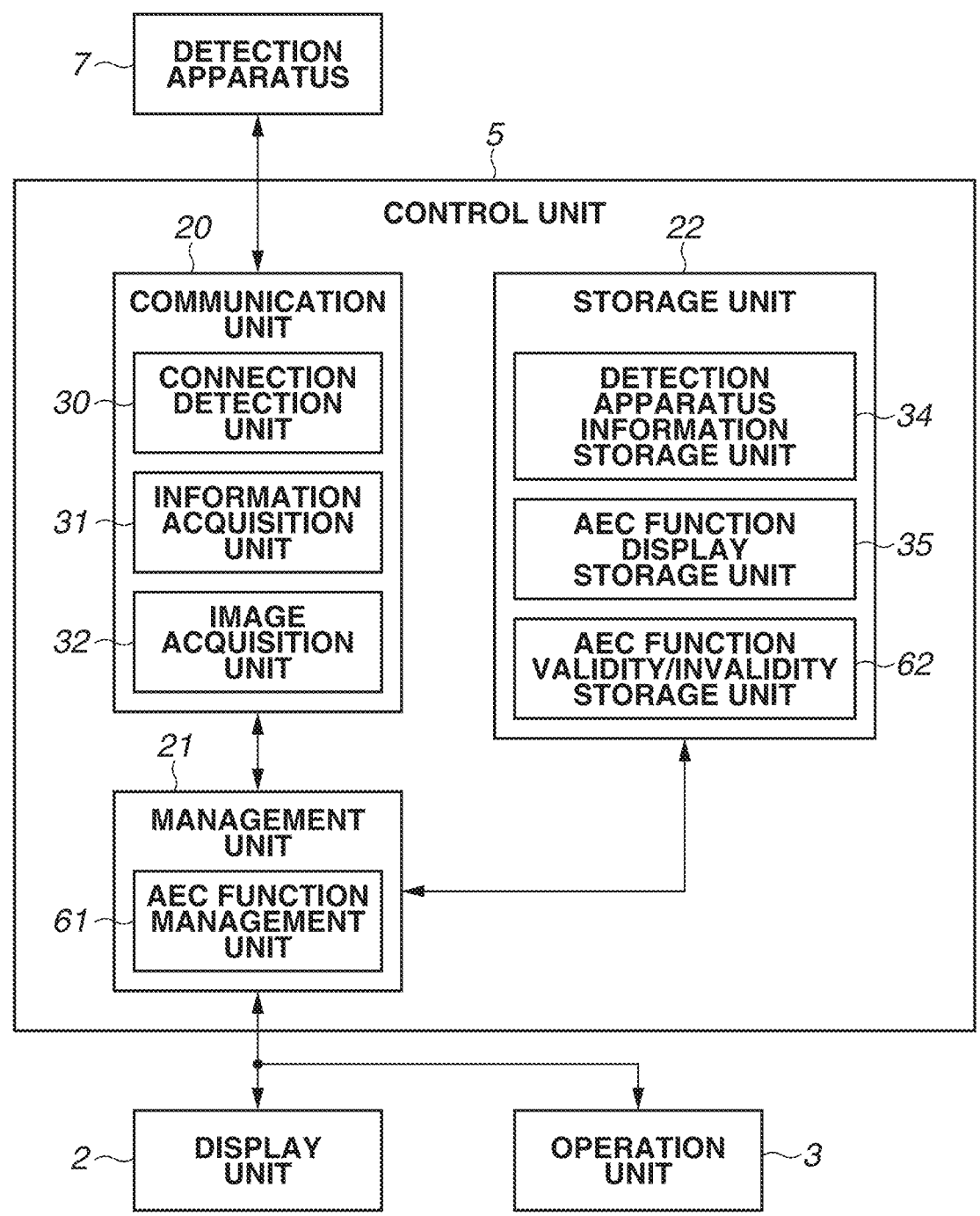
FIG. 14 is a block diagram illustrating an example of the control unit in the radiographing apparatus.

In the present exemplary embodiment, it is possible to notify the user that the AEC function is unusable in consideration of a state of validity/invalidity of the AEC function of the radiographing system. The fourth exemplary embodiment is different from the first and second exemplary embodiments in that, as illustrated in FIG. 14, an AEC function management unit 61 that determines contents to be displayed on the display unit 2 by comparing information on validity/invalidity of the AEC function acquired from an AEC function validity/invalidity storage unit 62 with information on presence/absence of the AEC function in the detection apparatus acquired from the detection apparatus information storage unit 34 is newly provided, and an alert about the AEC function can be issued in the radiographing system using the AEC function. The configurations other than the AEC function management unit 61 and the AEC function validity/invalidity storage unit 62 are similar to the configurations according to the first exemplary embodiment, and thus description is omitted.

Figure 15:
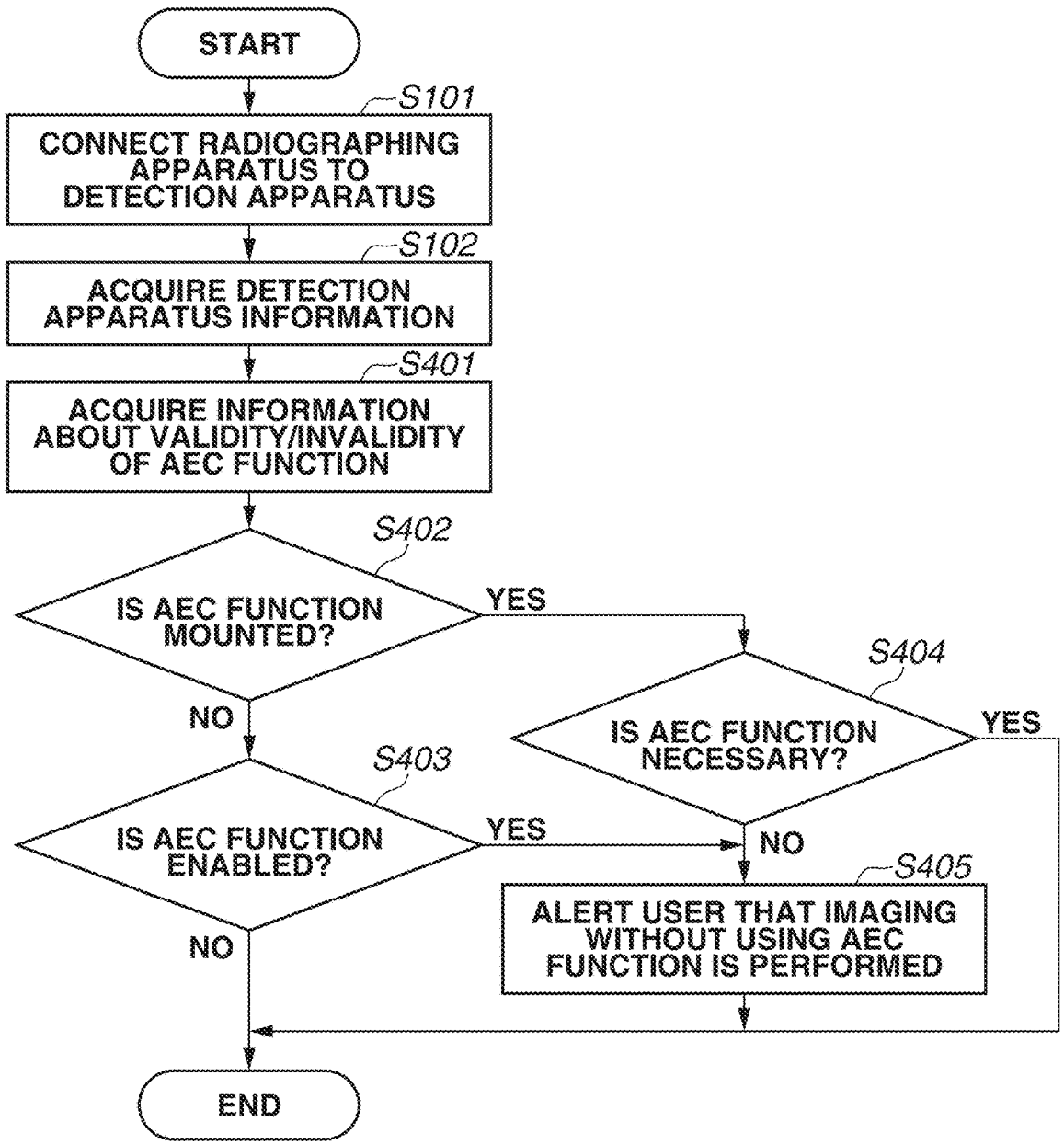
FIG. 15 is a flowchart illustrating an example of display control of an alert about the AEC function.

Processing performed by the AEC function management unit 61 and the AEC function validity/invalidity storage unit 62 is described with reference to a flowchart in FIG. 15, and FIGS. 16 and 17 described below. In the present exemplary embodiment, an example in which notification is performed before start of the inspection is described; however, the notification may be performed in a similar manner even after start of the inspection. The control performed before step S102 is the same as the control in the first exemplary embodiment, and thus description is omitted.

Figure 16:
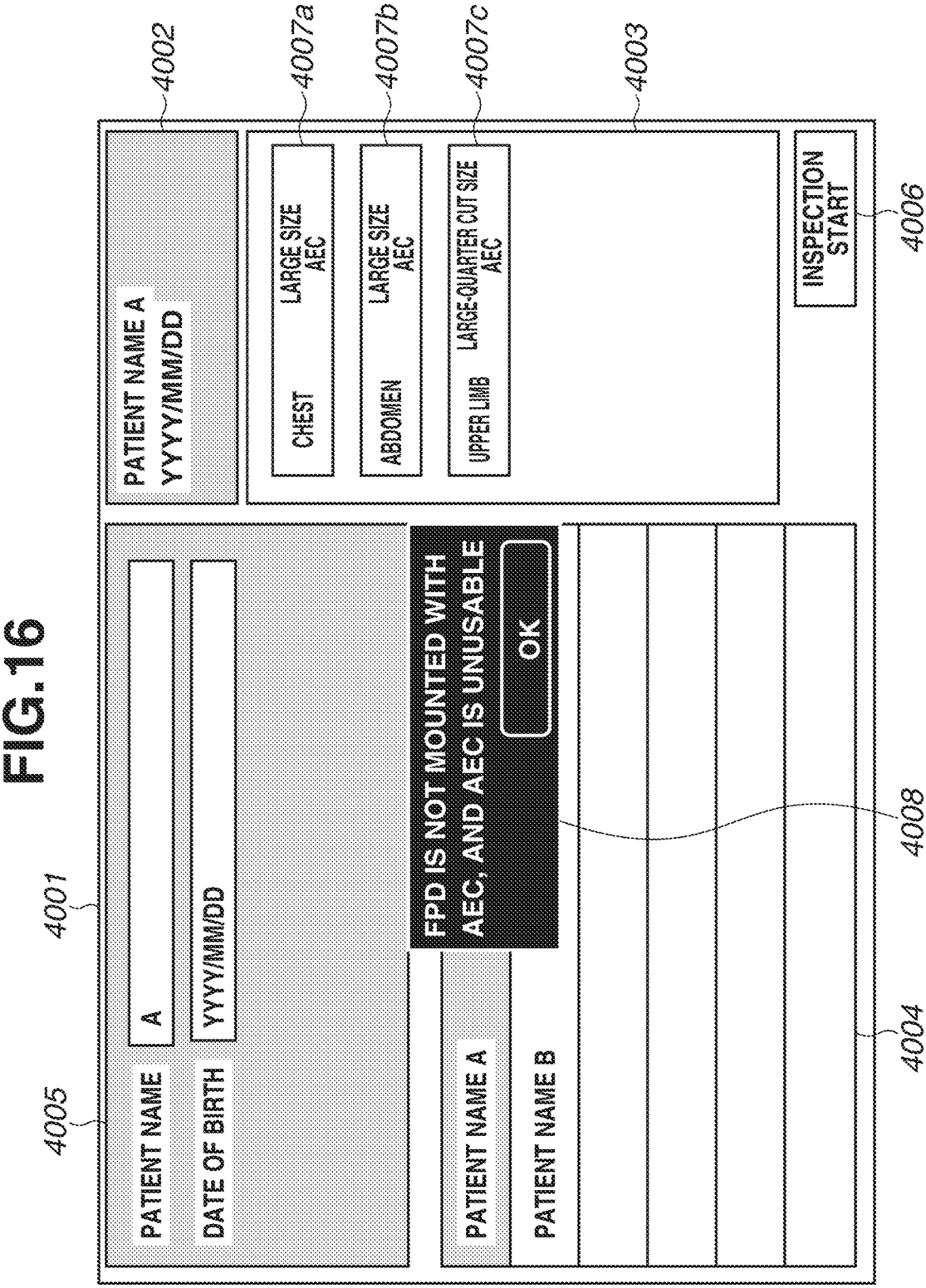
FIG. 16 is a diagram illustrating an example of the display unit in the radiographing apparatus.
Figure 17:
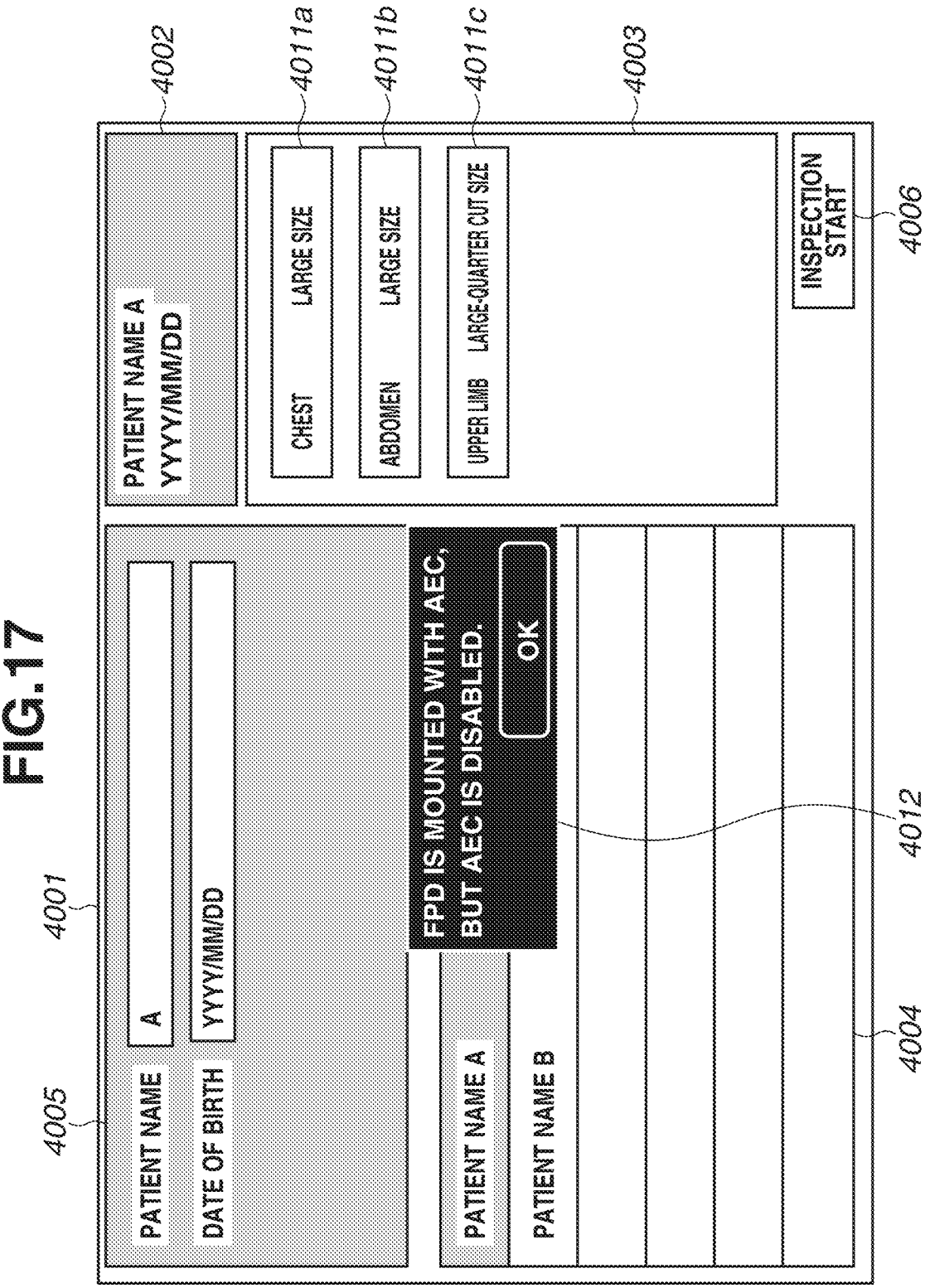
FIG. 17 is a diagram illustrating an example of the display unit in the radiographing apparatus.

FIGS. 16 and 17 each illustrate a display form of the display unit 2 before start of the inspection performed by the radiographing system according to the fourth exemplary embodiment of the present invention. The display form of the display unit 2 includes a radiation inspection list 4001, a patient information display field 4002 displaying information on a patient selected by the user and registered in an inspection list, an imaging information display field 4003, a radiation inspection list display field 4004, a patient information input field 4005, and an inspection start instruction portion 4006.

In FIG. 16, the imaging information display field 4003 displays imaging protocols (4007a, 4007b, and 4007c illustrated in FIG. 16) each displaying a site to be captured in the inspection, the information about the detection apparatus, and information indicating use/unuse of the AEC function. All of the imaging protocols use the AEC function.

In FIG. 17, the imaging information display field 4003 displays imaging protocols (4011a, 4011b, and 4011c illustrated in FIG. 17) each displaying a site to be captured in the inspection, the information about the detection apparatus, and information indicating use/unuse of the AEC function. All of the imaging protocols do not use the AEC function.

In step S401, the AEC function management unit 61 acquires information about validity/invalidity of the AEC function in the radiographing system. At this time, the information about validity/invalidity of the AEC function may be setting determined for each system. For example, the AEC function management unit 61 may acquire setting about validity/invalidity of the AEC function in the radiographing system, from the storage unit 22. Alternatively, the AEC function management unit 61 acquires imaging information from the storage unit 22, and may determine whether the AEC function is enabled or disabled based on the fact that the imaging information corresponding to the detection apparatus all indicate use (unuse) of the AEC function. The method of setting the information about validity/invalidity of the AEC function is illustrative, and is not limited to the above-described method.

In step S402, the AEC function management unit 61 acquires the display contents in the case where the AEC function is mounted and the display contents in the case where the AEC function is not mounted, from the AEC function display storage unit 35, and determines the contents to be displayed on the display unit 2.

In a case where the detection apparatus 7 is not mounted with the AEC function and the AEC function is enabled (NO in step S402 and YES in step S403), the processing proceeds to step S405. In step S405, a notification to alert the user that the AEC function is unusable is displayed on the display unit 2. For example, in step S405, as illustrated in an alert display field 4008 in FIG. 16, a message "FPD is not mounted with AEC, and AEC is unusable." is displayed to alert the user that imaging without using the AEC function is continued. At this time, for example, a message "To use AEC, please prepare FPD mounted with AEC or separate AEC sensor, and connect FPD again." may be displayed, as an alert, to propose a method to the user.

In a case where the detection apparatus 7 is mounted with the AEC function and the AEC function is disabled (YES in step S402 and NO in step S404), the processing proceeds to step S405. In step S405, a notification to alert the user that the AEC function is unusable is displayed on the display unit 2. For example, as illustrated in an alert display field 4012 in FIG. 17, a message "FPD is mounted with AEC, but AEC function is disabled." is displayed to alert the user that imaging without using the AEC function is continued. At this time, for example, a message "To use AEC, please enable AEC function." may be displayed, as an alert, to propose a method to the user. The alert displayed at this time may be closed when a predetermined time has elapsed. Alternatively, an OK button may be displayed as illustrated in FIG. 16 and FIG. 17, and the alert may be hidden in response to selection by the user. Further alternatively, the alert may be hidden when the AEC function becomes usable.

In a case where an alert is displayed in the fourth exemplary embodiment, the second and third exemplary embodiments may be omitted without being performed.

According to the present exemplary embodiment, in the radiographing system in which validity/invalidity of the AEC function is different between the detection apparatus and the radiographing system, it is possible to reduce possibility that the radiography is performed without using the AEC function by notifying the user that the AEC function is unusable in consideration of the state of validity/invalidity of the AEC function in the radiographing system.

The present invention can be realized by supplying a program realizing one or more functions of the above-described exemplary embodiments to a system or an apparatus via a network or a storage medium, and causing one or more processors in a computer of the system or the apparatus to read out and execute the program. Further, the present invention can be realized by a circuit realizing one or more functions.

The processor or the circuit may include a central processing unit (CPU), a micro processing unit (MPU), a graphics processing unit (GPU), an application specific integrated circuit (ASIC), or a field programmable gate array (FPGA). Further, the processor or the circuit may include a digital signal processor (DSP), a dataflow processor (DFP), or a neural processing unit (NPU).

The radiographing system according to each of the above-described exemplary embodiments may be realized as a single apparatus, or a plurality of apparatuses may be communicably combined to perform the above-described processing. Both of these are included in the exemplary embodiments of the present invention. A common server apparatus or a server group may perform the above-described processing. The plurality of apparatuses configuring the radiographing system is not necessarily present in the same facility or the same country as long as the plurality of apparatuses can communicate with one another at a predetermined communication rate.

The exemplary embodiments of the present invention include a mode in which a program of software realizing the functions of the above-described exemplary embodiments is supplied to a system or an apparatus, and a computer of the system or the apparatus reads out and execute codes of the supplied program.

The program codes installed in the computer in order to realize the processing according to the exemplary embodiments by the computer are included in the exemplary embodiments of the present invention, accordingly. Further, an operating system (OS) or the like operating on the computer may perform a part or all of the actual processing based on instructions included in the program read by the computer, and the functions of the above-described exemplary embodiments may also be realized by the processing.

The present invention is not limited to the above-described exemplary embodiments. Various modifications (including organic combinations of exemplary embodiments), for example, application not only to imaging of a still image but also to imaging of a moving image can be made based on the spirit of the present invention, and the modifications are not excluded from the scope of the present invention.

In other words, configurations obtained by combining the above-described exemplary embodiments are all included in the exemplary embodiments of the present invention.

According to the exemplary embodiments of the present invention, it is possible to perform imaging using the AEC function as intended by the user in the radiographing system performing the AEC imaging.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-090314, filed May 28, 2021, which is hereby incorporated by reference herein in its entirety.

What is claimed is:

1. A radiographing system including a radiation generation apparatus emitting a radiation, a radiation detection apparatus detecting the radiation to generate a radiographic image, and a radiographing apparatus controlling operation of the radiation detection apparatus by communicating with the radiation detection apparatus, the radiographing system comprising:
   an acquisition unit configured to acquire information about the radiation detection apparatus; and
   a determination unit configured to determine whether the radiation detection apparatus includes an automatic exposure control (AEC) function, based on the information about the radiation detection apparatus acquired by the acquisition unit.

2. The radiographing system according to claim 1, further comprising a display control unit configured to display, in a case where the determination unit determines that the radiation detection apparatus does not include the AEC function, at least one of a notification that the radiation detection apparatus does not include the AEC function and a notification that imaging is unperformable.

3. The radiographing system according to claim 2, wherein the display control unit displays the notification that the radiation detection apparatus does not include the AEC function, by graying out positional information on lighting fields of the radiation detection apparatus.

4. The radiographing system according to claim 2, wherein the display control unit displays the notification that the radiation detection apparatus does not include the AEC function, by pop-up display.

5. The radiographing system according to claim 4, wherein the display control unit displays a button to select whether to continue imaging.

6. The radiographing system according to claim 2, wherein, in a case where a predetermined time has elapsed after the display control unit displays the notification that the imaging is unperformable, the determination unit determines not to continue the imaging.

7. The radiographing system according to claim 4, further comprising a setting unit configured to set, in a case where the radiation detection apparatus does not include the AEC function, whether to perform the pop-up display.

8. The radiographing system according to claim 2, wherein, in a case where the radiation detection apparatus does not include the AEC function, the display control unit displays a notification to prompt switching to another radiation detection apparatus.

9. The radiographing system according to claim 8, wherein, in a case where the switched radiation detection apparatus is a detection apparatus mounted with the AEC function, the display control unit displays a notification that the imaging is performable.

10. The radiographing system according to claim 1, wherein the determination unit further determines whether the AEC function of the radiation detection apparatus is enabled, and
wherein the display control unit displays an alert of continuation of the imaging, in at least one of a case where it is determined that the radiation detection apparatus does not include the AEC function and the AEC function of the radiation detection apparatus is enabled, and a case where it is determined that the radiation detection apparatus includes the AEC function and the AEC function of the radiation detection apparatus is disabled.

11. A radiographing apparatus, comprising:
an acquisition unit configured to acquire information about a radiation detection apparatus; and
a determination unit configured to determine whether the radiation detection apparatus includes an AEC function, based on the information about the radiation detection apparatus acquired by the acquisition unit.

12. A radiographing method using a radiographing system, the radiographing system including a radiation generation apparatus emitting a radiation, a radiation detection apparatus detecting the radiation to generate a radiographic image, and a radiographing apparatus controlling operation of the radiation detection apparatus by communicating with the radiation detection apparatus, the method comprising:
acquiring information about the radiation detection apparatus; and
determining whether the radiation detection apparatus includes an AEC function, based on the acquired information about the radiation detection apparatus.

13. A non-transitory computer-readable storage medium that stores a program causing a computer to perform the radiographing method according to claim 12.

* * * * *